United States Patent [19]

Buchholz et al.

[11] Patent Number: 5,665,876

[45] Date of Patent: Sep. 9, 1997

[54] 3-(AMINOACYL-AMINO)-SACCHARIDES AND PROCESSES FOR THEIR PREPARATION

[75] Inventors: Klaus Buchholz, Braunschweig; Martina Noll-Borchers, Muelheim an der Ruhr; Martina Pietsch, Duisburg, all of Germany

[73] Assignee: Verein der Zuckerindustrie, Bonn, Germany

[21] Appl. No.: 530,286

[22] PCT Filed: Apr. 28, 1994

[86] PCT No.: PCT/EP94/01339

§ 371 Date: Nov. 2, 1995

§ 102(e) Date: Nov. 2, 1995

[87] PCT Pub. No.: WO94/25474

PCT Pub. Date: Nov. 10, 1994

[30] Foreign Application Priority Data

May 3, 1993 [DE] Germany .................. 43 14 407.1

[51] Int. Cl.[6] .................. C07H 5/04; C07H 15/12; C07C 229/00
[52] U.S. Cl. .................. 536/29.1; 536/18.5; 536/18.7; 536/123.13; 562/433; 530/395
[58] Field of Search .................. 514/8, 23, 42, 514/53; 536/1.11, 4.1, 18.5, 18.7, 123, 123.13, 124, 29.1; 530/322, 395; 562/433

[56] References Cited

U.S. PATENT DOCUMENTS 4,472,379  9/1984  Suami et al. .................. 424/177
5,463,022  10/1995  Inoue et al. .................. 530/322

FOREIGN PATENT DOCUMENTS 399448  11/1990  European Pat. Off. .

OTHER PUBLICATIONS

Kochetkov et al., *Izv. Akad. Nauk SSR, Ser. Khim.*, vol. (2): 367–371, (1967).
Kunz, Synthese von Glycopeptiden, etc., 1987, 297–311.
Paulsen, Synthesen, Konformationen, etc., 1990, 851–867.
Kiyozumi, Eine Verbesserte, etc., 1970, 355–365.
Pietsch, Untersuchungen zu Stabilitat, etc., 1993, 70–73.
L'vov, 3-[(n-Acetyl-1-Seryl)Amino]-3,6-dideoxy, etc., 1982, 233–239.
Montreuil, Primary Structure of Glycoprotein Glycans, etc., Advances in Carbohydrate Chemistry and Biochemistry, vol. 37, 157–223.
Knirel, Somatic Antigens of Shigella, etc., 1988, 51–61.

*Primary Examiner*—John Kight
*Assistant Examiner*—Howard C. Lee
*Attorney, Agent, or Firm*—Foley & Lardner

[57] ABSTRACT

The invention pertains to 3-(aminoacyl-amino)-saccharides of the general formula (I),

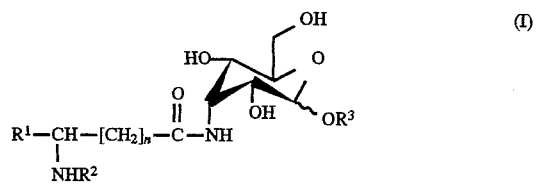

wherein R' is selected from the group consisting of hydrogen, a carboxyl group, a phenyl group and an alkyl group with 1–10 C-atoms which is optionally substituted by a phenyl, carboxyl, hydroxyl, mercapto or amino group, wherein said substitutents are optionally protected with protective groups; $R^2$ is selected from the group consisting of hydrogen, an amino protective group and a peptide group; and $R^3$ is hydrogen or a fructosyl radical; and n is 0 or 1. The invention also pertains to a method for preparing them.

6 Claims, No Drawings

3-(AMINOACYL-AMINO)-SACCHARIDES AND PROCESSES FOR THEIR PREPARATION

The invention concerns 3-(aminoacyl-amino)-saccharides and processes for their preparation from 3-amino-allo-saccharose.

Linkings of amino acids and saccharides are mainly present in glycopeptides and glycoproteins and, to a small extent, also in bacterial lipopolysaccharides. In the case of glycopeptides, it is a question of partial structures which occur as linkage region of saccharides and proteins in glycoproteins. Glycoproteins, which are to be found in soluble form in the blood and in numerous secrets, as well as in fixed form in membrane double layers, have, in recent times, achieved interest since their function has been recognised and investigated in biological control processes. In many cases, the carbohydrate side chains serve as recognition signal.

The nature of the covalent bonding between protein and carbohydrate side chain scarcely differs, however, in spite of the great number of naturally-occurring glycoproteins, which is caused by the biosynthesis of the glycoproteins. The two components are linked via a glycosidic bond, whereby one differentiates between N-glycoproteins and O-glycoproteins. In the case of the N-glycoproteins, the side chain amide group of an asparagine component is mostly linked β-N-glycosidically with 2-acetamido-2-desoxy-D-glucose. However, in addition, in recent times, there have also been found N-glycosyl sud N-galsctosyl structures. In the case of O-glycoproteins, there is mostly present an α-O-glycosidic linking of 2-acetamido-2-desoxy-D-galactose or a β-O-glycosidic linkage of D-xylose with a hydroxyl group of serine or threonine (H. Paulsen, Synthesen, Konformationen und Rötgen-struktureanalysen von Saccharidketteh der Core-Regionen von Glycoproteinen, Angew. Chem. 102 (1990) 851–867; H. Kurtz, Synthese von Glycopeptiden - Partialstrukturen biologischer Erkennungskomponenten, Angew. Chem. 99 (1987) 297–311; J. Montreuil, Primary Structure of Glycoprotein Glycans, Adv. Carbohydr. Chem. Biochem. 37 (1980) 157–223).

Individual amino acids have also been detected in lipopolysaccharides of bacterial origin which are linked via an amide formation with aminosugars, e.g. N-acetyl-glycine, which is bound via the amino group of 4-amino-4,6-didesoxy-D-glycopyranosyl radical to the O-specific side chain of the lipopolysaccharide of Shigella dysenteriae type 7 (Y. A. Knirel et al., Carbohydr. Res. 179 (1988), 51–60), or N-acetyl-L-serine which is bound via the amino group of the 3-amino-3,6-didesoxy-D-glucopyranosyl radical with the O-specific side chain of the lipopolysaccharide of Escherichia coli 0114 (V. L. L'vov et al., Carbohydr. Res. 112 (1983) 233–239). These substances act antigenically.

The invention refers to new 3-(aminoacyl-amino)-saccharides of the following formula I,

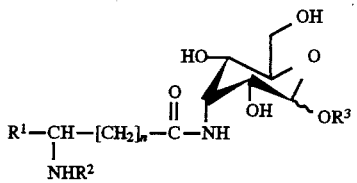

in which $R^1$ signifies hydrogen, a carboxyl group or a phenyl group or an alkyl group with 1–10 C-atoms which is possibly substituted by a phenyl, carboxyl, hydrozyl, mercapto or amino group, whereby the said substituents are possibly provided with protective groups, $R^2$ is hydrogen, an amino protective group usual in peptide chemistry or a peptide group and $R^3$ represents hydrogen or a fructosyl group, n=0 or 1, especially 3- (L-aminoacyl-amino)-D-allopyranosyl-β-D-fructofuranoside in the following designated as 3-(aminoacyl-amino)-allo-saccharose, and 3-(L-aminoacyl-amino)-D-allopyranose. Furthermore, the invention includes preparation processes for these materials starting from 3-amino-3-desoxy-D-allo-pyranosyl-β-D-fructofuranoside, briefly called 3-amino-allo-saccharose.

In the case of the 3-(aminoacyl-amino)-allo-saccharides according to the invention, it is a question of materials in which the carboxyl group of an amino acid is bound via an acid amide binding to the amino group of the 3-amino-allo-saccharose. Thus, in contra-distinction to the glycoproteins, these compounds contain no glycosidic bond between carbohydrate and amino acid but rather show a similar bonding structure to the above-mentioned lipopolysaccharides.

The 3-(aminoacyl-amino)-allo-saccharoses makes possible, with help of the methods of glycopeptide synthesis, the preparation of novel glycopeptides in which carbohydrate and protein are not bound via an N-glycosidic bond but rather via an acid amide bond. As starting compounds herefor are suitable especially acidic and basic amino acids since the amino acid residues in the amino acid saccharides in each case contain two functional groups, thus the peptide chain can be built up on two sides.

On the basis of the polyfunctionality of both starting components, the preparation of glycopeptides is very problematical and mostly requires the use of protective groups not only on the saccharide but also on the amino acid or the peptide. By the use of the 3-amino-allo-saccharose, which can be obtained without introduction of protective groups, it is now possible completely to omit protective groups for the synthesis of the 3-aminoacyl group in the saccharide part.

Via the splitting off of the fructosyl radical of the 3-(aminoacyl-amino)-allo-saccharoses, one can now also get to 3-(aminoacyl-amino)-alloses which, for their part, can serve for the preparation of glycopeptides. In this case, not only can a peptide chain be built up, in that further amino acids are attached to the amino acid radical, but also an oligosaccharide chain can be produced via the allose.

The compounds according to the invention, as well as derivatives produced therefrom, are useable in the interdisciplinary research and use, e.g. for the elucidation of the biological function of glycoproteins, for the induction of antibodies, for the research of the biological recognition and selectivity and for the development of pharmaceutically active materials, as well as as potential inhibitor for enzymes and micro-organisms.

The preparation of the 3-(L-aminoacyl)-amino-allo-saccharides starts from saccharose. Into this poly-functional molecule is introduced a keto group on the C-3 of the glucosyl radical, by means of a microbial oxidation with Agrobacterium tumefaciens, which subsequently can be selectively converted into an amino group by means of reductive amination, e.g. with ammonia, hydroxylamine or hydrazine by means of hydrogen and metal catalyst. After chromatographic purification, one obtains the amination product 3-amino-allo-saccharose (M. Pietsch, Dissertation TU Braunschweig, 1993). This synthesis route has already been described in similar way for the preparation of diamines from reduced saccharides in EP 0 399 448 A2.

The 3-amino-allo-saccharose now serves, for its part, as starting product far the 3-(aminoacyl-amino)-allo-saccharides. Surprisingly, the reaction takes place following the process described by M. Kiyozumi et al., Carbohydr.

Res. 14 (1970) 355–364. For this purpose, the 3-amino-allo-saccharose is reacted with N-terminally protected amino and diamino acids or with N- and C-terminally protected aminodicarboxylic acids or correspondingly protected peptides in a pyridine-water mixture with activation of the carboxyl function of the amino acid by means of N,N'-dicyclohexylcarbodiimide (DCC). Subsequently, the protective groups can be split off. A purification of the reaction products is possible e.g. by column chromatography. The structural verification of the purified substances takes place by means of $^{13}$C-NMR spectroscopy and fast atom bombardment mass spectrometry (FAB-MS).

As process for the preparation of the 3-(aminoacyl-amino)-saccharides, the following steps are taken:

1. Oxidation of saccharose e.g. with bacteria of the strain *Agrobacterium tumefaciens* NCPPB 396 to 3-keto-saccharose.

2. Reductive amination of the 3-keto-saccharose, as well as working up and separation of the resulting product mixture and isolation of the 3-amino-allo-saccharose.

3. N-acylation of the 3-amino-allosaccharose with amino acids or peptides with an activated carboxyl group, the other amino and carboxyl groups of which are possibly protected by means of protective groups usual in peptide chemistry.

4. Splitting off of one or more protective groups from the amino acid radical of the substance and/or of the fructosyl radical from the saccharose group, as well as isolation and purification of the product.

For the activation of the carboxyl group, dicyclohexylcarbodiimide (DCC) is preferred but 1,2-dihydro-2-ethoxyquinoline-1-carboxylic acid ethyl ester (EEDQ) is also useable as coupling resgent and other activated carboxyl groups, such as anhydrides, esters, azides or halides insofar as they do not react to a greater extent with the hydroxyl groups of the saccharide.

As amino protective groups, all groups known from peptide chemistry are useable which can again be split off in a gentle way. For example, there may be mentioned benzyloxycarbonyl (CBZ), t-butyloxycarbonyl (BOC) and triphenylmethyl (Trt), which are again split off by catalytic hydrogenation or acidic hydrolysis with hydrohalic acids but especially with trifluoroacetic acid.

As carboxyl protective groups are to mentioned, for example, alkyl esters and especially benzyl esters, which can be split off acidically or alkaline. Furthermore, the benzyl groups are to be removed especially gently by hydrogenolysis.

As amino acids are preferred the "natural" amino acids obtainable in large amounts by hydrolysis of proteins but, for certain purposes, synthetically prepared racemic or D-amino acids or amino acids which do not occur in nature can also be used. Furthermore, instead of an amino acid, a corresponding peptide can also be used.

The invention is explained in more detail by the following Examples.

EXAMPLE 1

Coupling of 3-amino-allo-saccharose with Amino Acids which Contain Pure Hydrocarbon Side Chains 3-(L-leucyl-amino)-allo-saccharose 200 mg 3-amino-allo-saccharose, together with 137 mg N-BOC-L-leucine (0.059 mmol), are dissolved in 13 ml of solvent (pyridine/H$_2$O, 4:1) and cooled in an icebath. Subsequently, with cooling, DCC (1.0 mmol dissolved in 0.5 ml solvent) is slowly added dropwise with stirring and cooling. After some time, the cooling is ended. After about 17 hours reaction time (with stirring), the reaction is broken off by addition of a drop of glacial acetic acid to the reaction mixture and, after 15 minutes stirring, the resulting insoluble dicyclohexylurea is filtered off. With the addition of toluene, the solvent is gently removed on a rotary evaporator (40° C., vacuum). The reaction product is transferred with water and diethyl ether into a separating funnel and the aqueous phase extracted several times with diethyl ether. The reaction product in the aqueous phase is freeze dried and the product purified by means of column chromatography (stat. phase:silica gel, eluent: acetic acid ethyl ester/ethanol/water, 5:3:1). One obtains 3-(N-t-BOC-L-leucyl-amino)-allo-saccharose in 35% yield.

$C_{23}H_{42}N_2O_{13}$ (M=554 g/mol)

$^{13}$C-NMR data (75.5 MHz, D$_2$O/acetone-d$_6$)=178.0 (C1"), 158.3 (C7"), 105.0 (C2'), 9.30 (C1), 82.6 (C5'), 82.2 (C8"), 77.5 (C3'), 74.6 (C4'), 69.4/66.1/65.7 (C2,4,5), 62.9/62.4 (C6',1'), 60.8 (C6), 55.3/53.4 (C3,2"), 40.8 (C3"), 28.5 (C9"–11"), 25.1 (C4"), 23.1 (C5",6").

FAB mass spectrum (pos. matrix glycerol):

m/z=555 [M+H]$^+$, 393 [M-fructosyl radical+H]$^+$, 761 [M=2 glycerol+Na]$^+$.

The splitting off of the t-butyloxycarbonyl (BOC) protective group takes place with 90% trifluoroacetic acid: For this purpose, the reaction product is dissolved in cold 90% trifluoroacetic acid and left to stand for 20 to 30 min at 4° C. Subsequently, the substance is precipitated out by addition of cold dry diethyl ether, filtered off and after-washed several times with diethyl ether. After column chromstographic purification, one obtains 3-(L-leucyl-amino)-allo-saccharose.

In the same way are prepared:

3-(N-BPC-L-alanyl-amino)-allo-saccharose
$C_{20}H_{36}N_2O_{13}$ 3

(M=512 g/mol)

$^{13}$C-NMR data (75.5 MHz, D$_2$O/acetone-d$_6$):

δ=170.8 (C1"), 154.9 (C4"), 104.2 (C2'), 91.6 (C1), 82.7 (C5'), 78.2 (C5"), 76.4 (C3'), 73.7 (C4'), 69.0/65.5/65.0 (C2,4,5), 61.8 (C6',1'), 60.1 (C6), 55.3 (C3),
49.5 (C2"), 28.1 (C6"–8"), 17.9 (C2").

3-(N-BOC-L-phenylalanyl-amino)-allo-saccharose
$C_{26}H_{40}N_2O_{13}$ (M=588 g/mol)

$^{13}$C-NMR data (75.5 MHz, D$_2$O/acetone-d$_6$:

δ=176.3 (C1"), 158.0 (C10"), 137.0 (C4"), 128.9/128.5/128.1 (C5"–9"), 104.5 (C2'), 92.5 (C1), 82.4 (C5'), 81.0 (C11"), 77.4 (C3'), 74.3 (C4'), 69.2/65.7/65.4 (C2,4,5), 66.5 (C6'), 62.4 (C1'), 60.5 (C6), 56.0/53.0 (C3,2"), 40.5 (C3"), 28.1 (C12"–14").

FAB mass spectrum (pos. matrix glycerol):

m/z=589 [M+H]$^+$, 427 [M-fructosyl radical+H], 611 [M+Na]$^+$.

The BOC group can also be split off from these compounds with trifluoroacetic acid.

EXAMPLE 2

Coupling of 3-amino-allo-saccharose with Acid and Basic Amino Acids 3-(4-L-aspartyl-amino) -allo-saccharose
$C_{16}H_{28}N_2O_{13}$ For this purpose, 150 mg 3-amino-allo-saccharose (0.44 mol), together with 142 mg N-t-BOC-L-aspartic acid benzyl ester, are dissolved in 13 ml of solvent (pyridine/H₂O, 4:1) and cooled in an icebath. Subsequently, with cooling, DCC (0.7 mmol dissolved in 0.5 ml of solvent) is slowly added dropwise with stirring and cooling. After some time, the cooling is ended. After about 17 hours reaction time (with stirring), the reaction is broken off by addition of a drop of glacial acetic acid to the reaction mixture and after 15 minutes stirring the resultant insoluble dicyclohexylures is filtered off. With the addition of toluene, the solvent is gently removed on a rotary evaporator (40° C. vacuum) The reaction product is transferred with water and diethyl ether into a separating funnel and the aqueous phase extracted several times with diethyl ether. The reaction product in the aqueous phase is freeze dried.

The splitting off of the benzyl protective group on the α-carboxyl group of the aspartic acid radical takes place by hydrogenolysis. Pot this purpose, the freeze-dried crude product (200 mg) is dissolved in 22 ml methanol in a three-necked flask with reflux cooler. The solution is treated with through-flowing hydrogen in the presence of a catalyst (palladium/active carbon, 10% Pd) with stirring for 3 h at a temperature of 30° to 40° C. after atmospheric oxygen had previously been displaced by nitrogen. After filtering off of the catalyst and removal of the solvent on a rotary evaporator (30° C. vacuum) the product is purified by means of column chromatography (stat. phase:silica gel, eluent:acetic acid ethyl ester/ethanol/water, 5:3:1). One obtains 3-(N-BOC-4-L-aspartyl-amino)-allo-sacaharose in 44% yield.

The splitting off of the BOC protective group takes place with 90% trifluoroscetic acid: for this purpose, the reaction product is dissolved in 0.7 ml cold 90% trifluoroscetic acid and left to stand for 15 to 20 min at 4° C. Subsequently, the substance is precipitated out by addition of cold dry diethyl ether, filtered off and after-washed several times with diethyl ether. After column chromatographic purification, one obtains 3-(4-L-aspartyl-amino)-allo-saccharose (77% yield).

$^{13}$C-NMR data (75.5 MHz, D₂O/acetone-d₆):

δ=174.7/174.1 (C1″,4″), 104.8 (C2′), 93.2 (C1), 82.7 (C5′), 77.3 (C3′), 74.9 (C4′), 69.6/66.2/65.9 (C2,4,5), 63.2/ 62.3 (C6′,1′), 61.1 (C6), 53.5/52.5 (C3,2″), 37.3 (C3″).

FAB mass spectrum (pos. matrix glycerol):

m/z - 457 [M+H]⁺, 295 [M-fructosyl radical+H]⁺, 913 [2M+H]⁺

In the same way is prepared 3-(Nα-BOC-N-CBZ-L-lysyl)-amino-allo-saccharose C₃₁H₄₉N₃O₁₄ (M=703 g/mol).

$^{13}$C-NMR date (75.5 MHz, D₂O/acetone-d₆):

δ=176.3 (C1″), 158.0/157.9 (C7″, 12″), 137.0 (C14″), 128.9/128.1/128.0 (C15″-19″), 104.5 (C2′), 92.5 (C1), 82.4 (C5′), 81.0 (C8″), 77.4 (C3′), 74.3 (C4′), 69.2/65.7/65.4 (C2,4,5), 66.5 (C6′), 62.4 (C1′), 60.5 (C6), 56.1/53.0 (C3, 2″), 40.5/40.6 (C3″-6″, 13″), 28.1 (C9″-11″).

FAB mass spectrum (pos. matrix glycerol):

m/z=726 [M+Na]⁺.

By splitting off of the protective groups with trifluoroacetic acid and catalytic hydrogenation, one obtains therefrom 3-(L-lysyl)-amino-allo-saccharose.

EXAMPLE 3

Hydrolyric Cleavage of the Glycoside Bond of the L-aspartyl-amino)-allo-saccharose By acid hydrolysis, one obtains from the 3-(4-L-aspartyl-amino)-allo-saccharose the D-(4-L-aspartyl-amino)-allose. For this purpose, 150 mg 3-(4-L-aspartyl-amino)-allo-saccharose are heated for 10 min to 60° C. with 5 ml hydrochloric acid (0.5N). Subsequently, the reaction solution is immediately cooled to 20° C. and neutralised with caustic soda solution. The separating off of the product from the reaction mixture takes place by means of preparative liquid chromatography on a cation exchanger in the Ca²⁺ form (eluent: H₂O, 70° C). 3-(4-L-aspartyl-amino)-allose is obtained with a yield of 80%, referred to the 3-(4-L-aspartyl-amino)-allo-saccharose used.

We claim:

1. A 3-(aminoacyl-amino)-saccharide of the general formula I,

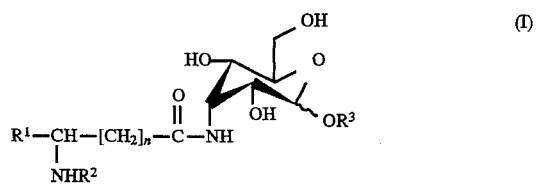

wherein R¹ is selected from the group consisting of hydrogen, a carboxyl group, a phenyl group and an alkyl group with 1–10 C-atoms which is optionally substituted by a phenyl, carboxyl, hydroxyl, mercapto or amino group, wherein said substitutents are optionally protected with protective groups; R² is selected from the group consisting of hydrogen, an amino protective group and a peptide group; and R³ is hydrogen or a fructosyl radical; and n is 0 or 1.

2. A saccharide according to claim 1, selected from the group of compounds consisting of:

3-(4-L-aspartyl-amino)-3-desoxy-D-allopyranosyl-β-D-fructofuranoside, 3-(L-alanyl-amino)-3-desoxy-D-allopyranosyl-β-D-fructofuranoside, 3-(L-leucyl-amino)-3-desoxy-D-allopyranosyl-β-D-fructofuranoside, 3-(L-lysyl-amino)-3-desoxy-D-allopyranosyl-β-D-fructofuranoside, 3-(L-phenylalanyl-amino)-3-desoxy-D-allopyranosyl-β-D-fructofuranoside, and 3-(4-L-aspartyl-amino)-3-desoxy-D-allopyranose.

3. A process for the preparation of a 3-(aminoacyl-amino)-saccharide according to claim 1, comprising reacting a 3-amino-3-desoxy-D-allopyranosyl-β-D-fructofuranoside with a compound of the formula II,

wherein R¹, R² and n are as defined as in claim 1 and X is an activating group, and optionally off one or both of the fructosyl group or protective groups present and isolating the resultant 3-(aminoacyl-amino)-saccharide.

4. The process according to claim 3, wherein said resultant 3-(aminoacyl-amino)-saccharide is purified chromatographically.

5. The process of claim 3, wherein the 3-(aminoacyl-amino)-saccharide produced is selected from the group of compounds consisting of:

3-(4-L-aspartyl-amino)-3 -desoxy-D-allopyranosyl-β-D-fructofuranoside, 3-(L-alanyl-amino)-3-desoxy-D-allopyranosyl-β-D-fructofuranoside, 3-(L-leucyl-amino)-3-desoxy-D-allopyranosyl-β-D-fructofuranoside, 3-(L-lysyl-amino)-3-desoxy-D-allopyranosyl-β-D-fructofuranoside, 3-(L-phenylalanyl-amino)-3-desoxy-D-allopyranosyl-β-D-fructofuranoside, and 3-(4-L-aspartyl-amino)-3-desoxy-D-allopyranose.

6. The process according to claim 3, wherein said resultant 3-(aminoacyl-amino)-saccharide is purified chromatographically.

* * * * *